United States Patent

Fleischmann

[11] Patent Number: 6,010,524
[45] Date of Patent: Jan. 4, 2000

[54] PROCESS AND DEVICE FOR STIMULATING THE FORMATION OF NEW TISSUES IN EXTENSIVE AND DEEP WOUNDS

[76] Inventor: Wim Fleischmann, Nelkenweg 15, D-89182 Bernstadt, Germany

[21] Appl. No.: 08/964,660

[22] Filed: Nov. 5, 1997

Related U.S. Application Data

[62] Division of application No. 08/663,050, filed as application No. PCT/DE94/01467, Dec. 12, 1994, Pat. No. 5,733,305.

[30] Foreign Application Priority Data

Dec. 13, 1993 [DE] Germany ............... 43 42 457

[51] Int. Cl.⁷ .................................. A61B 17/08
[52] U.S. Cl. ................ 606/213; 606/215; 606/216
[58] Field of Search ............... 606/213, 215, 606/216, 217, 218, 148, 151

[56] References Cited

U.S. PATENT DOCUMENTS

| | | | |
|---|---|---|---|
| 2,371,978 | 3/1945 | Perham | 128/335 |
| 4,702,251 | 10/1987 | Sheehan | 128/335 |
| 5,486,196 | 1/1996 | Hirshowitz et al. | 606/218 |
| 5,531,009 | 7/1996 | Frechet et al. | 623/15 |
| 5,556,428 | 9/1996 | Shah | 623/13 |
| 5,562,705 | 10/1996 | Whiteford | 606/215 |
| 5,571,138 | 11/1996 | Blomqvist et al. | 606/218 |
| 5,611,794 | 3/1997 | Sauer et al. | 606/8 |
| 5,618,310 | 4/1997 | Ger et al. | 606/216 |
| 5,723,009 | 3/1998 | Fretchet et al. | 623/15 |
| 5,759,193 | 6/1998 | Burbank et al. | 606/213 |

*Primary Examiner*—Michael Buiz
*Assistant Examiner*—Tina T. D Pham
*Attorney, Agent, or Firm*—Pendorf & Cutliff

[57] ABSTRACT

In order to stimulate the formation of new tissues in extensive and deep wounds, the tissues are eased by exerting a traction force on the tissue with a vertical force component in relation to the plane of the wound. If the wound is vacuum sealed by a plastic foil (F), traction may be exerted through the foil (F). If a distractor that acts in the plane of the wound is set at the wound edges, the vertical traction component may be exerted on the edges of the wound by this distractor. The vertical traction component is generated through turnbuckles (70).

18 Claims, 2 Drawing Sheets

PROCESS AND DEVICE FOR STIMULATING THE FORMATION OF NEW TISSUES IN EXTENSIVE AND DEEP WOUNDS

This is a divisional of application Ser. No. 08/663,050 filed Jun. 13, 1996, which issued as U.S. Pat. No. 5,733,305 on Mar. 31, 1998. Ser. No. 08/663,050 was filed as PCT/DE 94/01467, filed Dec. 12, 1994 and from German application No. P 43 42 457.0, filed Dec. 13, 1993.

BACKGROUND OF THE INVENTION

The invention concerns a process and a device for stimulation of the formation of new tissues in large surface area wounds and deep tissue defects according to the introductory portion of the independent patent claims.

DESCRIPTION OF THE RELATED ART

Large surface area wounds caused by open fractures or external influences are to a greater extent liable to disease causing agents, since the deepest tissue layers down to the damaged bone are exposed to the environment.

Even an infection by staphylo- or streptococci can be life threatening for the injured. The contamination of the large surface area wound by Proteus, Pseutonmas or Klebsiella leads as a rule to a life threatening septic condition. Further the healing process is burdened by the dying off of damaged tissue components. This highly toxic albumin decomposition product is discharged from the organism as a fluidized wound excrement. According to the degree of injury the injured may require more or less frequent extremely painful follow-up treatments of the wound.

For the operative care of large surface area wounds there has, in recent times, been employed a technique of vacuum sealing (for example 0093/09727). In accordance therewith, after the first operative care of the wound, the tissue defect or skin section and various tissue pockets are filled in with a layer of polyvinyl foam material, wherein in adjacent foam material layers so called Redon-drainages are incorporated directly into the foam material. Therein attention must be paid, that the drainage perforation does not come into contact with the soft parts, since they would form a tight suction seal upon application of a vacuum and their drainage function would be lost. The so applied layers of polyvinyl foam material are thereafter sealed with a transparent, water vapor permeable but bacterial non-transmissive polyurethane foil, such that the polyurethane foil covers the wound as well as the undamaged skin surrounding the edge of the wound. After connection of the Redon-drainages to a vacuum system the wound discharge is suctioned off and at the same time a more intensive contact between the wound and the foam material is achieved, which, as has been shown through experience - substantially improves the cleansing of the wound and the new formation of granulation tissues.

It has however been shown, that the atmospheric pressure resting upon the tissue worsens the perfusion of blood in the boarder area of the wound and in many cases leads to muscle atrophy and to devitalization of the tissue regions. In the damaged tissue frequently chambers are formed, in which toxic albumen decomposition products collect, which can lead to a life threatening septic condition in the injured patient. The recovery can—if at all—be achieved with difficult, with operative measures associated with prolonged, cost intensive and painful wound therapy which supplementally burdens the organism.

It is further known (for example from U.S. Pat. No. 4,896,680 and U.S. Pat. No. 5,263,971), to draw the peripheries of the wound of a large surface area wound together by means of a so-called skin-distractor, in order to be able to suture the wound peripheries to each other. The skin-distractor engages in the cutis or dermis with two distractor segments on respectively opposing wound peripheries. The distractor segments are drawn together via a spiral spindle. The drawing together is accomplished in successive steps, whereby the skin is stretched to the limits of its viscoelastic extensibility. The known skin distractor accomplishes pulling forces only in the plane of the wound field, in order to pull the peripheries of the wound together utilizing the viscoelastic properties of the skin. A formation of new tissues is not possible herewith and not intended.

SUMMARY OF THE INVENTION

The object of the invention is comprised therein, to improve the treatment of a tissue defect by insuring the tissue vitality and advancing the formation of new tissues, to avoid the complications frequently associated with large surface area wounds and in particular to create an environment so that the growing together of the corium or dermis is substantially improved.

This object is accomplished by a process for stimulation of formation of new tissue in large surface area and deep wounds, the process comprising exerting a negative pressure upon the tissue, wherein for attaining the negative pressure a pull force acting at an angle to the plane of the wound field is exercised upon the tissue. The object is further accomplished by a device for stimulation of formation of new tissue in large surface area and deep wounds, the device including a plastic foil (F) which covers over the wound and the wound edge, the device further including at least one pull anchor (21) which engages on the plastic foil (F) in the area of the wound field, which is connected via positioning means (70) with a mounting support (distractor 50) which spans over the wound field.

The invention is based upon the realization, that a pulling tension acting on the tissue in the wound area with a component perpendicular to the plane of the would surface during tissue new formation results in a continuous reduction in size of the wound with a simultaneous formation of a uniformly structured granulation field and filling up of the tissue defect and thus leads to a rapid wound reduction in size. Thereby the blood perfusion through the tissue is substantially improved, whereby an expediting of the healing process results and in many cases follow up operations for definitive wound closing can be dispensed with.

With a vacuum sealing of the wound with a plastic foil, there is achieved upon the tissue defect an accelerated tissue regeneration by a bringing to bear of pulling forces over the plastic foil or the foam material layers provided under the plastic foil. In addition it is also possible to ensure a continuation of tissue profusion through a prolonged post-traumatic and post-operative edema phase. Also, the protected wound remains for a longer period of time well conditioned against secondary infections. The so-treated large surface area and deep tissue defects are therefore more thoroughly detoxified, and are better perfused, whereby the mortality is substantially reduced.

For the drawing and growing together of the cutis a skin distractor can be employed, which draws together the wound edges horizontally, that is, in the plane of the wound surface. Upon this skin distractor there is supplementally exercised a perpendicular to the wound surface (vertical) force component, in order to unburden the tissue in the area of the wound edges and to stimulate tissue new formation in the area of the cutis. In contrast to the known skin distractors the wound edges are herein drawn together only very slowly (over a period of days or weeks), so that the skin is not viscoelastically stretched but rather the wound edges grow together by new tissue formation.

The growing together of the cutis can be targeted and controlled by adjustment according to empirical observations of the distraction—or pull force both horizontally upon the wound edges as well as also vertically upon the tissue defect, so that also in large surface area tissue defects the pitting remains small and post-traumatic damage appearance can be avoided.

Finally, the painful changing of bandages can be reduced by utilization of the inventive process. Overall a reduction of the healing time occurs.

BRIEF DESCRIPTION OF THE DRAWINGS

The invention is described below by means of the illustrative examples shown schematically in the drawings. There are shown.

DETAILED DESCRIPTION OF THE DRAWINGS

Figure 1:
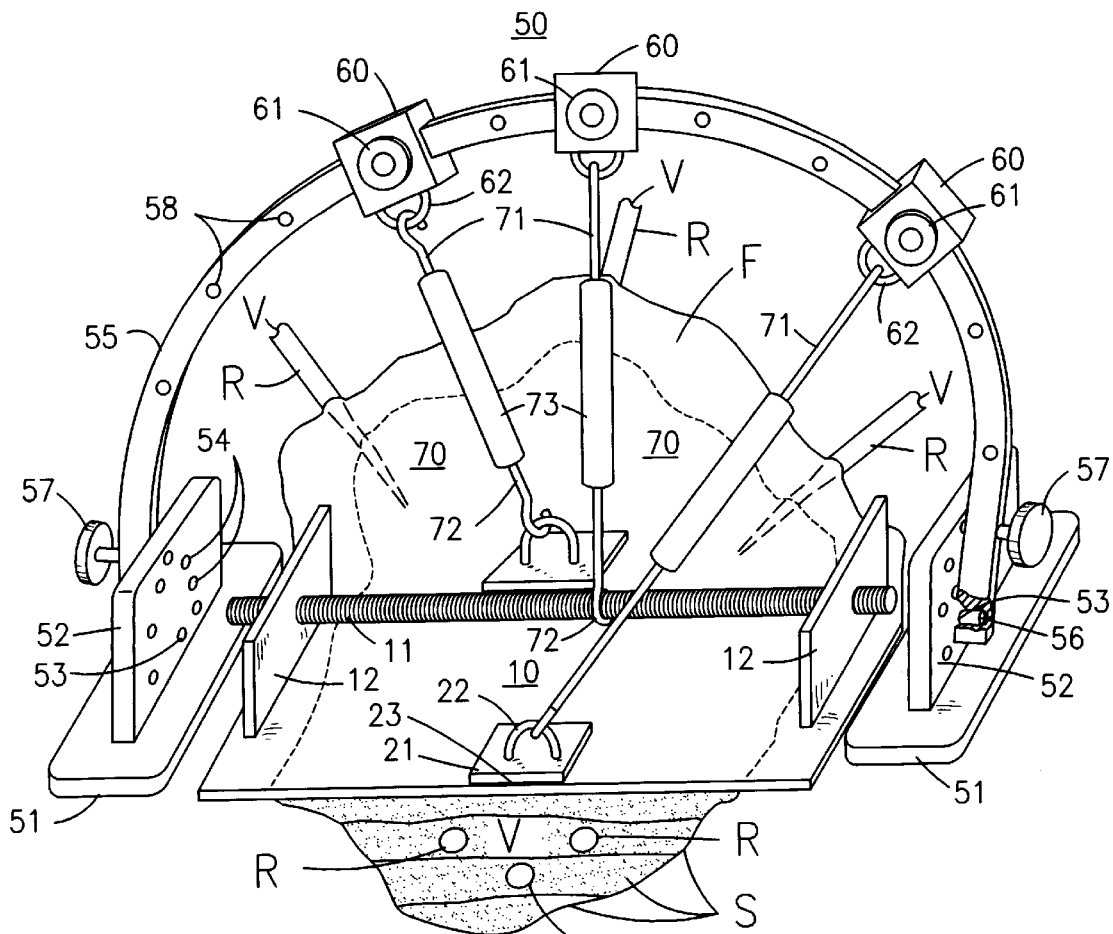
FIG. 1 a device according to the invention for stimulation of the superficial and deeper tissue formation in large surface area and deep tissue defects, with a horizontal and vertical acting distractor in perspective representation.

FIG. 1 shows the basic arrangement of the device for formation of new tissue in a large surface area, deep wound W, which is dressed with a polyvinyl foam material layer S, in which drainage tube R is introduced, which is in communication with a not shown vacuum system. The polyvinyl foam layers S are covered over by a large surface area, transparent, water vapor permeable but bacteria nontransmissive polyurethane cover foil F which substantially covers over the wound edges, which after application of a vacuum V via the drainage tube R is pressed by atmospheric pressure against the wound edges and forms a tight seal and so seals the wound.

Further, a vertical acting distractor 50 is provided. For this one or more anchors are provided on the cover foil F, which are comprised of plates 21 which lie flat upon the surface of the cover layer and are preferably capable of being cut to size, on one side of which eyelets 22 are provided standing approximately perpendicular, and upon the opposite side an adhesive layer 23 is provided, by means of which the plates 22 laying flat upon the cover foil F can be secured by adhering.

Alternatively or additionally to the plates 21 adhered to the cover foil F, anchors can be provided on the polyvinyl foam layer S, which are comprised of posts embedded in and projecting horizontally out of the polyvinyl foam material layer S, or gratings provided under the polyvinyl foam material layer S, or the like.

On the respectively oppositely lying areas of the wound edge there are provided base support elements 51 for supporting or bracing the distractor 50, each of which exhibits in the middle thereof a support mount 52, in which a cylindrical borehole 53 is provided centrally. Spaced apart from the borehole 53 threaded bores 54 are provided in the support mount 52. The base support elements are preferably fixed to the body by means of sleeves, longuettes or preformed shells, whereby the base support elements are glued onto the sleeves, longuettes or shells according to the requirements of the injury to be treated.

A semi-circular shaped bow 55 is associated with the support mounts 52, which by means of inward facing bolts 56 provided on the ends thereof—of which only the right one is shown, rests in the borehole 53 of the support mount 52. The bow 55 is provided on each of its ends, spaced apart from bolt 56, respectively with a knurled screw 57, with which the bow 55 can be secured to the support mount 52 by screwing in of the knurled screws 57 in the threaded boreholes 54 in various angular positions. The bow 55 is further provided with a series of axial threaded boreholes 58. On the bow 55 slidable members 60 are slidably mounted, which in the middle respectively are provided with a knurled screw 61, with which the slidable members 60 can be secured in position by screwing in of the knurled screw 61 in one of the threaded boreholes 58 of the bow 55. Further, each slidable member 60 is provided on its wound facing side with a eyelet 62.

In the eyelets 62 of the slidable members 60 and the eyelets 22 of the pull anchors 20 there are engaged respectively hooks 71, 72 of a turnbuckle 70. If the anchor is provided in or under the polyvinyl foam layer S, then the turnbuckles engage preferably via a draw string onto these anchors. The draw string is sealingly guided through the polyvinyl foam layer. For the purpose of the adjustment of the draw force the hooks 71, 72 of the turnbuckle 70 are respectively circumscribed by a right and left thread exhibiting turnbuckle middle part 73.

Corresponding to the particular characteristics of the wound of the injured the bow 55 can be tilted around the bolt 56 and be secured to the support mount 52 by means of the knurled screws 57. The slide members 60 can be so arranged upon the bow 55, so that the pull force can be maintained for the guidance of the stimulation of the formation of the new tissue in the necessary direction, and by means of the turnbuckle 70 then the desired pull force can be exercised targeted upon a specific wound area or upon the entire wound, in order to effectively direct a revitalization in particular of deep lying tissue regions.

On the respective oppositely lying sides of the wound edge a horizontal acting distractor 10 can be provided after removal of the vacuum sealing, which encompasses two distractor segments 12, which by means of a threaded spindle 11 can be moved towards or apart from each other according to the inclination of the threaded spindle. The distractor segment 12 exhibits spurs 20, which are introduced into the cutis in the area of the wound edge.

A pull anchor 70, which with its hook 71 is hung into the eyelet 62 of a slidable member 60, is with its other hook 72 hooked into the threaded spindle 11 of the horizontal operating distractor 10. By means of the turnbuckle 70 a vertical pull force, adjustable by means of the turnbuckle middle part 73, is exerted upon the threaded spindle 11 and therewith the distractor segment 12. Supplemental to the pull force exercised horizontally to the plane of the wound surface via the threaded spindle 11 there is produced thereby a pull force component operating vertically upon the wound surface. These vertical working pull force components facilitate the new tissue formation in the area of the wound edge.

According to the requirements of the wound there can also be provided a multiplicity of vertical and/or horizontal operating distractors in modular fashion or in the form of a universal distractor with a plurality of pull anchors 20, so that via the provided turnbuckles 70 targeted pull forces can be exercised upon the wound in any desired direction.

The base support elements 51 are thus abutments of the vertical operating distractor 50 for transmission of the pull forces of the distractor 50. For adaptation to the spherical characteristics in the region bordering about the tissue defect, an underlying substrate for fixing the distractor device can be provided between the base support element 51 and uninjured tissue, which makes possible the even distribution of the pull forces acting there as pressure forces. Herewith the base support elements 51 of the device can be brought to bear upon a conventional plaster, upon synthetic material bandages, or upon impact and break resistant, hypo-allergenic polyvinyl alcohol products which can be formed into the desired form.

It is foreseeable, that the vertical operating pull forces need not necessarily be supported or abutted against the body of the patient via the support elements. Alternatively thereto, the vertically working distractor 50, onto which the turnbuckles 70 are engaged, can be secured to a gallows or a similar device mounted on the bed of the patient.

With the horizontal working distractor 10 a horizontal operating pull distraction force is borought to bear, via the threaded spindle 11 which draws the distractor segment 12 towards each other, which helps to guide the growing together of the corium.

Herewith the pull forces brought to bear via the horizontal operating distractor 10 and the vertical operating distractor 50 supplement or compliment each other.

Figure 2:
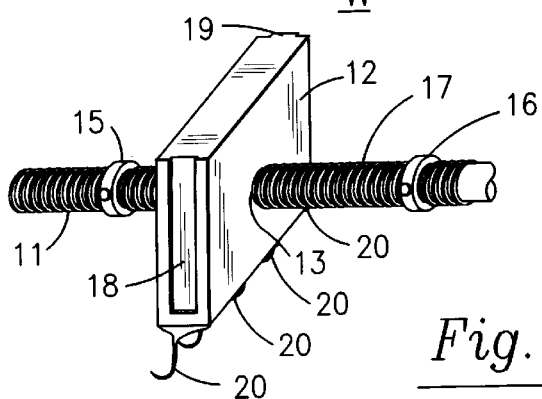
FIGS. 2 through 4 distractor segments of the distractor according to the invention with various barb shapes in extendable modular construction form and FIG. 5 a further example of the distractor for stimulation of new formation of tissue.
Figure 3:
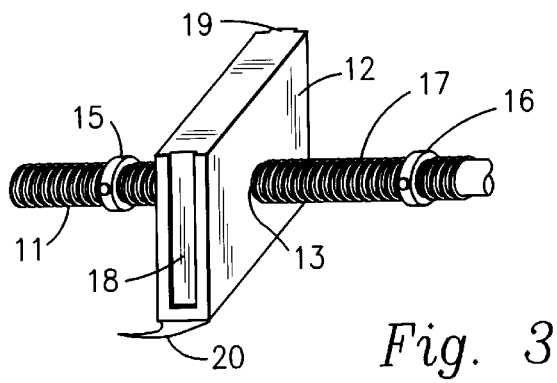
Figure 4:
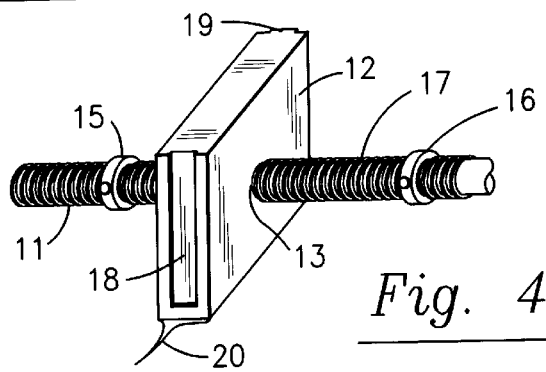

As can be seen from FIGS. 2, 3 and 4, the distractor segment 12 of the distractor 10 are provided with a central borehole 13, through which the threaded spindle 11 is introduced. Provided upon the threaded spindle on the side of the distractor segment 12 facing toward the wound there is respectively a threaded nut 15 serving as a functional stop or abutment. On the side of this distractor segment 12 facing away from the wound there is provided upon the threaded spindle 11 a pressure spring 17, which is so acted upon by an associated threaded nut 16 adjustably provided on the threaded spindle 11, that the spring force, which acts upon the distractor segment 12, is variable.

The distractor segments 12 and 13 exhibit in their side edges respectively upon the one side a notch 18 and upon the oppositely lying side a key 19. The lower edge which faces the wound in contrast is provided with a number of needle like thorns or spurs 20. The design of the spurs 20 is dependent upon the external surface of area of use of the body. Thus FIG. 2 shows hook shaped, FIG. 3 shows claw shaped and FIG. 4 shows spurs oriented approximately 20° in the direction towards the wound. The spurs are introduced in the cutis in the area of the edge of the wound.

This design of the distractor segment 12 makes possible the modular construction of a distractor 10 adapted to the particular wound to be stretched by joining together of a number of distractor segments 12, wherein these are connected to each other by introduction of the notch 18 of the one distractor segment in the key 19 of the adjacent distractor segment be connected with each other.

Figure 5:
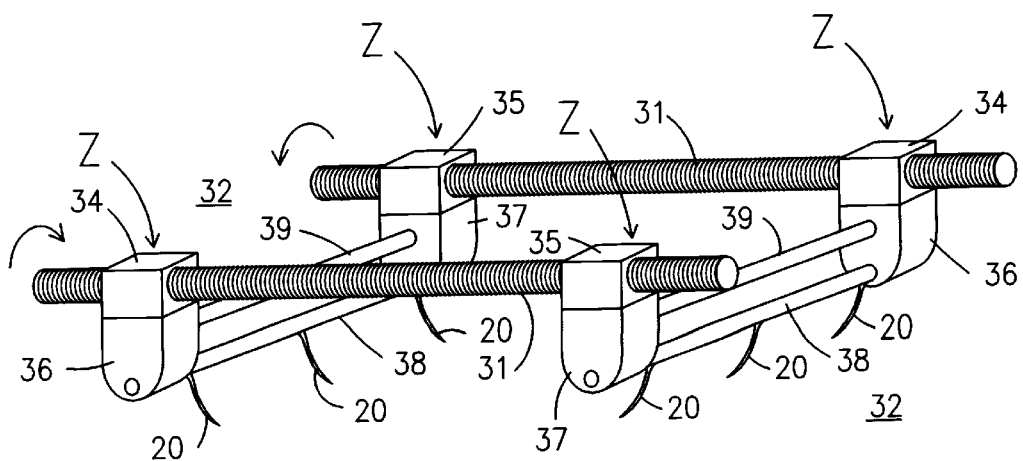

The further illustrative embodiment of a distractor as shown in FIG. 5 encompasses two threaded spindles 31 with two distractor segments 32 moveable towards and apart from each other. The threaded spindles 31 exhibit respectively one of the ends a right-hand and the other end a left-hand threading. As further shown in FIG. 5, the right- and left-handed threading of the threading spindle 31 which serves for the adjustment of the pull force are respectively in operative association with corresponding threaded boreholes in base or footing 34 and 35, to which respectively about the vertical axis Z pivotably associated turn segments 36 and 37 are provided. The turn segments 36 and 37 are connected force and form fast by means of two bendable struts 38 and 39. Each strut 38 carries a row of needle-like spurs 20 directed approximately 20° to the Z-axis toward the wound.

All construction elements of the device are produced from titanium or osteosynthetic steel. There can however also be employed synthetic materials or carbon fiber laminate materials which meet the requirements.

Through use of the above-described device for stimulation of the new formation of tissues in large surface area and deep tissue defects, the mortality as well as the frequency of occurrence of complications is substantially reduced.

Beyond this the described device according to the invention makes possible the controlling and minimization of formation of scars.

Finally as a further consequence of utilization of the described device the total recuperation period is reduced.

I claim:

1. Device for stimulation of formation of new tissue in large surface area and deep wounds, said device including a plastic foil (F) which covers over the wound and the wound edge, said device further including at least one pull anchor (21) which engages on the plastic foil (F) in the area of the wound field, which is connected via positioning means (70) with a mounting support (distractor 50) which spans over the wound field.

2. Device according to claim 1, further including at least one open porous foam material layer (S) adapted for laying into the wound field, into which foam material layer (S) at least one drainage tube (R) is introduced, said drainage tube (R) attachable to a suction source, and wherein said the plastic foil (F) covers the foam material layer (S).

3. Device according to claim 1, wherein said pull anchor (21) is connected to the surface of the plastic foil (F).

4. Device according to claim 3, wherein said pull anchor (21) is comprised of a flat plate, upon one side of which a perpendicular eyelet (22) is provided, and upon the other side of which an adhesive layer is provided for adhesively adhering said pull anchor to the plastic foil (F).

5. Device according to claim 1, wherein the mounting support takes the form of an arc shaped bow (55), which is supported on both ends thereof.

6. Device according to claim 5, wherein the bow (55) is, with its ends, pivotably and securably mounted in support mounts.

7. Device according to claim 5, wherein slide members (16) are provided slidably and securably upon the bow (55), which serve for attachment of the positioning means (70).

8. Device according to claim 1, wherein the positioning means are constructed as lengthwise adjustable turnbuckles (70).

9. Device for stimulation of the formation of new tissue in large surface area and deep wounds, said device including a plastic foil (F) which seals and covers the wound and the wound edge and including at least one open porous foam material layer (S) adapted for laying into the wound field, wherein at least one pull anchor engages on one of the foam material layers (S) in the area of the wound field and wherein the pull anchor is connected, via adjusting means (70) which is guided sealingly through the plastic foil, to a mounting system which spans over the wound field (distractor 50).

10. Device according to claim 9, wherein the adjusting means (70) engages with the foam material layer (S) via a draw string, wherein said draw string engages a pull anchor which is embedded under the foam material layer (S) or which lies under the foam material layer (S) oriented perpendicular to the direction of drawing of the draw string or is tied in to the foam material layer (S).

11. Device according to claim 9, wherein the penetration position of the adjusting means, or, as the case may be, draw string, through the plastic foil (F) is sealed by a hydrogel mass.

12. Device for stimulation of the formation of new tissues in large surface area and deep wounds, said device comprising at least:

two distractor elements (12, 32) which engage the cutis close to the wound edge, a bridge which spans over the wound, and adjusting means (70) connected to said distractor element and said bridge, for exercising a vertical traction component on said cutis, wherein said two distractor elements (12, 32) of a distractor (10) are positioned on opposite sides of the wound edge and are displaceable towards and away from each other, wherein the distractor elements (12, 32) are moveable with respect to each other by means of threading (11, 31), and wherein the distractor elements (12) respectively comprise at least one cylindrical borehole (13), in which a threaded rod (11) is longitudinally slidably introduced, upon which a winding nut (15) serving as a stop for the distractor element (12) is provided, while upon the opposite side of the distractor element (12) a further winding nut (16) is provided which causes force to bear via a pressure spring (17).

13. Device according to claim 12, wherein the distractor segment (12, 32) engages in the cutis with spurs (20).

14. Device according to claim 13, wherein the distractor elements (12, 32) are provided on their lower side with a row of spurs (20).

15. Device according to claim 12, wherein two distractor elements (12) with their respective threaded positioning means form a distractor module (10).

16. Device according to claim 15, wherein the distractor elements (12) are modularly engageable with each other by means of notches and protrusions (18, 19) respectively formed on their face sides.

17. Device for stimulation of the formation of new tissues in large surface area and deep wounds, said device comprising at least:

distractor elements (12, 32) which engage the cutis close to the wound edge, a bridge which spans over the wound, and adjusting means (70) connected to said distractor elements and said bridge, for exercising a vertical traction component on said cutis, wherein the distractor elements (12, 32) are moveable with respect to each other by means of threading (11, 31), and wherein the distractor elements (12) respectively comprise at least one threaded borehole and wherein a threaded rod engages in the bore holes of the distractor (12) with left and right threading for effect relative movement of the distractor elements (12).

18. Device according to claim 17, wherein the distractor element (32) comprises two threaded segments (36, 37), which are connected via struts or braces (38, 39), and wherein the threaded segments (36, 37) are mounted pivotable about the Z-axis in bases (34, 35), which are provided with the threaded bores.

* * * * *